United States Patent [19]

Timberlake et al.

[11] Patent Number: 5,605,820
[45] Date of Patent: Feb. 25, 1997

[54] **PRODUCTION OF STRAINS HAVING BIOLOGICAL ACTIVITIES BY SEXUAL CROSSES BETWEEN VEGETATIVELY INCOMPATIBLE STRAINS OF *ASPERGILLUS NIDULANS***

[75] Inventors: William E. Timberlake, Bolton; T. Vance Morgan, Natick, both of Mass.

[73] Assignee: Chemgenics Pharmaceuticals, Inc., Cambridge, Mass.

[21] Appl. No.: 264,952

[22] Filed: Jun. 23, 1994

[51] Int. Cl.$^6$ .............................. C12N 15/00; C12N 1/14
[52] U.S. Cl. .................... 435/172.2; 435/172.1; 435/172.3; 435/254.1; 435/256.1
[58] Field of Search ............................ 435/254.1, 256.1, 435/172.3, 172.2, 172.1

[56] References Cited

U.S. PATENT DOCUMENTS 5,229,291  7/1993  Nielsen ............................ 435/252.2

OTHER PUBLICATIONS

Aharonowitz and Cohen, Bioactive Microbial Secondary Metabolites, Biotechnology: Potentials and Limitations, ed. S. Silver, pp. 99–112, Dahlem Konferenzen 1986. Berlin, Heidelberg, New York, Tokyo: Springer–Verlag.
Anwar et al., Analysis of Heterokaryon Incompatibility Between Heterokaryon–Compatibility (h–c) groups R and GL Provides Evidence that . . . Incompatibility in *Aspergillus nidulans*, J. Gen. Microbiol. 139:1599–1603, 1993.
Bailey, Toward a Science of Metabolic Engineering, Science 252: 1668–1675, 1991.
Carpenter et al., Epidermal Growth Factor Stimulates Phosphorylation in Membrane Preparations In Vitro, Nature 276:409–410, 1978.
Dales and Croft, Investigation of the *het* Genes that Control Heterokaryon Incompatibility Between Members of Heterokaryon–compatibility groups A and G1 of *Aspergillus nidulans*, J. Gen. Microbiol. 136: 1717–1724, 1990.
Franco and Coutinho, Detection of Novel Secondary Metabolites, Critical Reviews in Biotechnology 11:193–276, 1991.
Geiser et al., Sexual Origins of British *Aspergillus nidulans* Isolates, Proc. Natl. Acad. Sci. USA 91:2349–2352, 1994.
Gilman et al., Pharmacodynamics: Mechanisms of Drug Action . . . Concentration and Effect, The Pharmacological Basis of Therapeutics (Goodman and Gilman, eds.) MacMillian Publishing, New York, 1980, pp. 28–39.
Gotoh et al., Studies on a New Immunoactive Peptide, FK–156 II. Fermentation, Extraction and Chemical and Biological Characterization, J. Antibiotics 35:1286–1292, 1982.

Grindle, Heterokaryon Compatibility of Closely Related Wild Isolates of *Aspergillus nidulans*, Heredity 18:397–405, 1963.
Grindle, Heterokaryon Compatibility of Unrelated Strains in the *Aspergillus nidulans* Group, Heredity 18:191–204, 1963.
Hawksworth, The Fungal Dimension of Biodiversity: Magnitude, Significance, and Conservation, Mycol. Res. 95:641–652, 1991.
Hotta et al., New Antibiotic–producing Streptomycetes, Selected by Antibiotic Resistance as a Marker II. Features of a New Antibiotic–Producing Clone Obtained After Fusion Treatment, J. Antibiotics 38:64–69, 1985.
Hutchinson et al., Drug Discovery and Development Through the Genetic Engineering of Antibiotic–Producing Microorganisms, J. Med. Chem. 32:929–937, 1989.
Koller et al., Ebelactones Inhibit Cutinases Produced by Fungal Pathogens, J. Antibiotics 43:734–735, 1990.
Klaassen, Principles of Toxicology, The Pharmacological Basis of Therapeutics, (Goodman and Gilman, eds.) MacMillian Publishing, New York, 1980, pp. 1602–1614.
Kosemura et al., The Structures of Citreohybridone A and B Novel Sesterterpenoid–type Metabolites of a Hybrid . . . Derived from *Penicillium Citreo–Viride* B. IFO 6200 and 4692, Tetrahedron Letters 32:3543–3546, 1991.
Lai et al., Novel Curvularin–type Metabolites of a Hybrid Strain ME 0005 Derived from *Penicillium Citreo–Viride* B. IFO 6200 and 4692, Tetrahedron Letters 30:2241–2244, 1989.
Lai et al., New Metabolites of Two Hybrid Strains ME 0004 and 0005 Derived from *Penicillium citreo–viride* B. IFO 6200 and 4692, Chemistry Letters pp. 589–592, 1990.
Merrick, Hybridization and Selection for Increased Penicillin Titre in Wild–type Isolates of *Aspergillus nidulans*, J. Gen. Microbiol. 91:278–286, 1975.
Merrick, The Inheritance of Penicillin Titre in Crosses Between Lines of *Aspergillus nidulans* Selected for Increased Productivity, J. Gen. Microbiol. 91:287–294, 1975.
Porter & Fox, Diversity of Microbial Products—Discovery and Application, Pestic. Sci. 39:161–168, 1993.
Selitrennikoff, Use of a Temperature–Sensitive, Protoplast––Forming *Neurospora crassa* Strain for the Detection of Antifungal Antibiotics, Antimicrob. Agents Chemother. 23:757–765, 1983.

(List continued on next page.)

*Primary Examiner*—Irene Marx
*Attorney, Agent, or Firm*—Fish & Richardson P.C.

[57] ABSTRACT

The invention features methods of generating a new biological activity involving carrying out a sexual cross between two vegetatively incompatible parental fungal strains, and screening the progeny of the sexual cross for the production of the biological activity.

1 Claim, 4 Drawing Sheets

OTHER PUBLICATIONS

Sleckman et al., Expression and Function of CD4 in a Murine T–cell Hybridoma, Nature 328:351–353, 1987.

Sonnenbichler et al., Further Metabolites from Dual Cultures of the Antagonistic Basidiomycetes *Heterobasidion annosum* and *Gloeophyllum abietinum*, Bio. Chem. Hoppe–Seyler 374:467–473, 1993.

Tanida et al., Tan–999 and Tan–1030A, New Indolocarbazole Alkaloids with Macrophage–Activating Properties, J. Antibiotics 42:1619–1630, 1989.

Tomich, *Streptomyces* Cloning: Possible Construction of Novel Compounds and Regulation of Antibiotic Biosynthetic Genes, Antimicrobial Agents & Chemo. 32:1472–1476, 1988.

Umezawa et al., Ebelactone, An Inhibitor of Esterase, Produced by Actinomycetes, J. Antibiotics 33:1594–1596, 1980.

Yamashita et al., New Antibiotic–Producing Streptomycetes, Selected by Antibiotic Resistance as a Marker, J. Antibiotics, 38:58–63, 1985.

Smith et al, "The Filamentous Fungi.", vol. 2, 1979 pp. 434–435.

Jinks et al., *Heredity*, 1966, vol. 21, pp. 227–239.

Jaynes et al., *Phytopathology*, 70:453–456, 1980.

Holt et al., *Nature*, vol. 219, 1969, pp. 636–637.

Strausbaugh et al., *Genetics*, vol. 82, 1992, pp. 61–68.

PRODUCTION OF STRAINS HAVING BIOLOGICAL ACTIVITIES BY SEXUAL CROSSES BETWEEN VEGETATIVELY INCOMPATIBLE STRAINS OF *ASPERGILLUS NIDULANS*

BACKGROUND OF THE INVENTION

This invention relates to methods of generating novel progeny from fungi to produce new biological activities not detectable in the parents.

Secondary metabolites produced by microorganisms, such as fungi, reflect a wide variety of chemical structures affecting numerous biological activities in different classes of organisms, including both prokaryotes (bacteria) and eukaryotes (animals, plants, and insects). Antibiotics constitute the largest group of known bioactive secondary metabolites, acting on such diverse processes as cell wall synthesis, DNA replication, and protein synthesis. In addition to their use as antibiotics, secondary metabolites are being successfully developed and used in agriculture as pesticides, herbicides, and anti-parasitic compounds, and in treating non-infectious human diseases as inhibitors of enzyme activity, as immunomodulators, and as anti-hypersensitivities. There are a number of reasons for the urgency in the expansion and intensification of the search for new useful secondary metabolites. Among these reasons are the need for less toxic, more potent antibiotics, the evolving resistance to existing antibiotics, emergence of new viral diseases, and related factors of concern in agriculture.

It is estimated that there are a minimum of 1.5 million species of fungi. About 70,000 species of fungi have been described in the literature (Hawksworth, Mycol. Res. 95:441–452, 1991), and only about 5,000 of these have been documented as producers of secondary metabolites (Porter et al., Pestic. Sci. 39:161–168, 1993). These observations have exciting implications for the discovery of large numbers of new bioactive secondary metabolites from known fungi, and further indicate that the world's undiscovered fungi can be viewed as a massive potential resource of new secondary metabolites.

SUMMARY OF THE INVENTION

We have shown that carrying out sexual crosses between vegetatively incompatible (VgI) organisms can lead to the production of biological activities in the progeny of the crosses that are not detectable in either of the VgI parental strains, using the same detection method used to detect the activity in the progeny.

Accordingly, the invention features a method of generating a new biological activity. In this method, a sexual cross is carried out between two VgI parental fungal strains. The progeny of the sexual cross are then screened for the production of a biological activity which is not detectable in either of the two parental strains using the same detection method used in the screening of progeny. As used herein, the term "vegetatively incompatible" (VgI) is used to describe strains which possess a mechanism (a vegetative incompatibility system) which prevents the exchange between them of genetic information by parasexual means between different VgI groups. The term "parasexual" is used to describe reproduction that results in recombination of genes from different individuals, but does not involve meiosis and formation of a zygote, as in sexual reproduction. The term "progeny" refers to any of the descendants of a sexual cross, including F1 and F2 generations, etc. As used herein, a biological activity is described as "new" if it is detectable in a progeny of a cross between VgI organisms, but not in either parent using the same detection method.

Organisms that can be used in the methods of the invention include any fungal species in which parasexual genetic exchange is regulated by a vegetative incompatibility system, and in which sexual reproduction occurs. Preferred organisms include vegetatively incompatible strains of filamentous ascomycetes (e.g., *Aspergillus nidulans*), filamentous basidiomycetes, and yeast. The screening can be carried out using (1) an extract of a fermentation of the progeny, including both the fermentation broth and the progeny, (2) an extract of the fermentation broth alone, or (3) an extract of the progeny alone.

Biological activities that can be screened for in the method of the invention include, but are not limited to, antibiotics (e.g., anti-fungal and anti-bacterial activities, which can be directed against, e.g., *Candida albicans* and *Bacillus subtilis*, respectively), cell growth inhibitors, enzyme inhibitors, immunosuppressives, anti-hypertensives, anti-hypersensitivities, microtubule inhibitors, pesticides, herbicides, and anti-parasitics.

An advantageous feature of the invention is that it allows the production and propagation of novel strains of organisms that would not normally be generated and/or survive in nature. These novel strains produce biological activities that are not detectable in either of the parental strains from which they were generated, using the same detection method. Thus, the method of the invention allows the production of a greater diversity of biological activities than those that are present in organisms that exist in nature.

Other features and advantages of the invention will become apparent from the following detailed description, the drawings, and the claims.

DETAILED DESCRIPTION

The drawings are first described.

Drawings FIG. 1A is a representation of asexual reproduction. Asexual, or clonal, reproduction takes place by mitotic division, and does not involve the union of individuals or germ cells. FIG. 1B is a representation of parasexual reproduction resulting from a rare fusion of haploid nuclei. A and B represent two VgI genes, each with 2 alleles (A/a and B/b). Only when the alleles of both genes are identical can a heterokaryon be formed. In the heterokaryon, the different nuclei can fuse and reassort their genes via a parasexual mechanism consisting of rare recombination events followed by haploidization through the loss of one of the two homologs of each chromosome (aneuploidy).

FIG. 3 is a schematic representation showing the development of fungal genotypes surviving in nature. The figure depicts the sexual mating between two VgI strains to form recombinant progeny and the ability to culture these progeny in the laboratory, while most of these progeny would be selected against in nature. The sexual cross between VgI parents AB and A'B' leads to formation of progeny (indicated by the large number of small arrows at the top of the figure), many of which do not survive in nature (indicated by the small number of arrows at the bottom of the figure). In the methods of the present invention, the initial progeny from the sexual cross, including those organisms that might not survive in nature, are recovered and propagated in the laboratory.

PRODUCTION OF NEW BIOLOGICAL ACTIVITIES

The present invention provides methods for generating novel progeny, which may produce new secondary metabolites with biological activities, by carrying out sexual crosses between VgI strains. VgI strains may encounter one another in nature, but they will rarely mate. Thus, the method of the present invention allows recombinant progeny to be generated that are not likely to be produced in nature. These novel recombinant strains have altered secondary metabolism, and produce new biological activities not present in their parents. Thus, carrying out crosses between VgI strains within various fungal species provides a novel source for the detection of new biological activities.

Reproduction in Fungi

Ascomycetous fungi (Ascomycetes) constitute the largest group of fungi, and these organisms reproduce by asexual, parasexual, and sexual means (FIGS. 1A, 1B, and 2).

Parasexual Reproduction

Parasexual reproduction in Ascomycetes, as well as in Basidiomycetes, is controlled by a VgI system. The salient feature of VgI is that it is controlled by a number of genes (8–9), each having 2 or more alleles (e.g., $a^1/a^2/a^3$), and that a successful genetic exchange will result only in those cases in which the alleles of VgI genes of the two parents are alike (Dales et al., J. Gen. Microbiol. 136:1717–1724, 1990). If cells of strains of different VgI groups fuse, the VgI recognition system does not allow development of the heterokaryon, and the fused cell dies. VgI was first reported for *Aspergillus nidulans* by Grindle (Grindle, Heredity 18:191–204, 1963, ibid. 397–405). In *A. nidulans*, VgI is controlled by the activities of at least eight genes, with at least 2 alleles in each locus (the het genes; Anwar et al., J. Gen. Microbiol. 139:1599–1603, 1993). The implication of this complexity is that two isolates in nature will be alike so that they may exchange genetic information. Therefore, *A. nidulans* strains exist in nature as isolated clones having different genetic compositions (Geiser et al., Proc. Natl. Acad. Sci. USA 91:2349–2352, 1994).

Reassortment of genetic traits as a means for the generation of diversity requires the interaction between two strains that are unlike in genetic aspects other than VgI, and the exchange of cytoplasm and nuclei between the mates, which results in formation of a heterokaryon consisting of cells containing haploid nuclei from both parental strains. When such heterokaryons are formed, their nuclei occasionally will undergo fusion to form a diploid nucleus which undergoes reassortment of chromosomes in a parasexual cycle (the frequency of fusion between haploid nuclei is approximately 1 for every $10^6$ heterokaryons formed) (FIG. 1B). These nuclei are unstable and undergo gradual reduction in the number of chromosomes, eventually leading back to the haploid state. During this process, reassortment of chromosomes can take place so that the new haploid nuclei contain chromosomes from each of the parental strains. In addition, in the diploid nuclei, mitotic recombination may occur prior to the reduction of the number of chromosomes.

Sexual Reproduction

Hyphae consist of cells with haploid nuclei and are involved in sexual reproduction. Fusion and heterokaryon formation between different strains involves physical contact between the reproductive cells of the strains, and formation of an anastomosis between the interacting strains, resulting in the nuclei and cytoplasm of both strains being in the same cell. The haploid nuclei fuse to form a zygote, which proceeds through meiosis, leading to the formation of haploid ascospores. Since recombination occurs regularly and frequently during meiosis, the high frequency of recombination and reassortment among the 8–9 genes contributing to VgI, with 2 or more alleles each, has the potential to give rise to greater than 500 different VgI haplotypes. These haplotypes are potentially a large source for new diversity in strains of fungi.

It has recently been shown that novel VgI groups of *A. nidulans* arise in nature by rare sexual matings that occur between members of different VgI groups (Geiser et al., Proc. Natl. Acad. Sci. USA 91:2349–2352, 1994). However, only 20 different VgI groups of *N. nidulans* are currently known, out of more than 100 British isolates that have been studied (ibid, 1994). Based on these findings, the number of VgI haplotypes that actually occur in nature can be estimated. It is clear that the number of types found in nature is far lower than the number that can be generated. These results indicate that many of the progeny of these strains may have reduced fitness and thus cannot survive in nature. FIG. 3 shows how, over time, (days, decades, or millennia) progeny from a sexual cross could disappear in nature, due to selective pressures.

In the present invention, we have shown that strains from different VgI groups (i.e., vegetatively incompatible strains) are fully capable of meiotic outcrossing in the laboratory. The progeny of these crosses may be less vigorous than their parents. The ability to manage these crosses in the laboratory allows recovery of the diversity of individuals that would not survive in nature, and the generation of progeny that are not likely to be produced in nature due to the environmental isolation of the parental strains. These isolates can serve as a source for new biological activities.

We present data that shows that the progeny of crosses between members of different VgI groups produce new biological activities, not detectable in either of the parents, using the same assay as that used to detect the activity in the progeny. Accordingly, the invention provides methods for producing novel progeny with new biological activities. In these methods, clones from different VgI groups are mated sexually and random recombinant ascospores are plated. The resultant clones are then cultured, stored, and fermented. The fermentations are then tested for the presence of desired biological activities.

Organisms

Organisms that can be used in the methods of the invention include any fungal species in which parasexual genetic exchange is regulated by a vegetative incompatibility system, and in which there is a sexual cycle. The specimens that can be used include those from any known laboratory stocks and those collected from nature. Fungi are collected from nature by plating samples of, e.g., soil, leaf litter, humus, or other substrates. Collected fungi are first classified by gross morphological analysis using, for example, microscopic examination of their spore structure or mycelial development. The fungi can be further characterized using standard classification methods, including the use of known molecular genetic probes, eventually leading to genus and species assignments.

The fungi can be placed into VgI groups by pairwise testing, using standard methods (see, e.g., Merrick, J. Gen. Microbiology 91:278–286, 1975). Sexual crosses between strains of different VgI groups (and/or different natural habitats) are then carried out using standard methods (e.g., see Example below).

Screening Progeny for the Production of New Biological Activities

Progeny from the sexual crosses are isolated, and fermentations are carried out using standard methods. Extracts are prepared from either the total fermentation, including the broth and the fungi (e.g., WBBEs, see below), from the fermentation broth alone, or from the isolated fungi alone. Extractions are carried out using solvents, such as ethyl acetate, acetone, or butanol, in standard methods.

The extracts are subjected to screens for useful biological activities which include, but are not limited to, antibiotics (against, e.g., bacteria, fungi, and viruses), pesticides (e.g., antihelminthics, insecticides, acaricides, anticoccidials, antitreponemals, and antitrichomonals), herbicides, anti-tumor agents, cardiovascular active agents (e.g., vasodilators, calcium channel blockers, fibrinolytic agents, and free radical scavengers), modulators of microtubule dynamics, anti-inflammatory agents, immunomodulators, anti-hypersensitivities, receptor-ligand interaction modulators, enzyme activity modulators, hypolipidemic agents, and cell growth modulators, using standard methods in the art (see, e.g., Franco et al., Crit. Rev. in Biotech. 11(3):193–276, 1991, and references therein) which can involve the use of biochemical assays, cell or tissue culture assays, and animal model systems. Several of these assays are described further below.

Antibiotic Activities

Anti-bacterial activities can be identified using a number of standard assays known in the art. For example, a culture of bacteria, such as a lawn of *Bacillus subtilis*, can be contacted with a sample of a fermentation extract, and the areas of lysis characterized, as described in detail below (see Example, below). In addition to detecting general effects on bacterial growth and viability, the screening methods of the invention can involve assaying for effects on bacteria-specific structures, enzymes, or processes.

A large number of antifungal compounds have been identified using classic approaches, e.g., evaluating fermentation samples in primary tests directly against a range of filamentous fungi and yeasts, e.g., *Candida albicans*, grown in agar plates, or in some cases, directly against phytopathogenic infestations (Bastide et al., Mircen J. Appl. Microbiol. Biotechnol. 2:453, 1986; Haruo, Gendai Kagaku Zokan 9:16, 1987). Very few antifungal antibiotic secondary metabolites have found utility in therapy because of toxicity problems. Selective action against fungi is difficult to achieve considering the many physiological features common to both fungi and infected hosts. Several examples of fungi-specific targets include chitin and glucan synthases (Selitrennikoff et al., Antimicrob. Agents Chemother. 23:757, 1983; Kirsch et al., J. Antibiot. 39:1620, 1986; Denisot et al., Abstract 9th Int. Symp. Future Trends in Chemother., Geneva, Mar. 26 to 28, 1990, 47), and cutinases (Köller et al., J. Antibiot., 43:734, 1990; Umezawa et al., J. Antibiot. 33:1594, 1980).

Anti-viral antibiotics can be identified by screening for inhibitors of virus-specific enzymes, such as retroviral reverse transcriptases. Other virus-specific processes, such as viral uncoating, viral receptor binding, and cell fusion (e.g., syncytium formation caused by HIV) can also be targeted in the screening methods of the invention.

Anti-Tumor Activities

To identify anti-tumor activities, cultured tumor cell lines or cultured tumors can be contacted with the extracts, and effects on cell growth and viability monitored. Another approach involves screening for extracts which induce differentiation of tumor cells, which causes these cells to lose their tumorigenicity (Franco et al., Crit. Rev. in Biotech. 11(3):193–276, 1991).

Enzymes can also be used as targets for identifying anti-tumor activities. Enzymes that have been successfully employed as targets in the search for anti-tumor agents include protein tyrosine kinases, which are components of signal transduction pathways regulated by a number of oncogenes (Carpenter et al., Nature 276:409, 1978; Franco et al., Crit. Rev. in Biotech. 11(3):193–276, 1991), phosphatidylinositol kinase, spermidine synthase, and topoisomerases (Franco et al. Crit. Rev. in Biotech. 11(3):193–276, 1991). As the differences between tumor and non-tumor cells become more apparent, tumor cell-specific targets can be used in the screens in order to identify activities that are not toxic to the patient.

Extracts that exhibit anti-tumor activities in biochemical and cell culture assays can be tested further in appropriate animal model systems.

Immunosuppressive Activities

Several fungal secondary metabolites have been shown to have immunosuppressive activities, and are therefore useful in preventing rejections of transplanted tissues and organs. Immunosuppressive activities can be identified using a number of standard methods in the art, including the mixed lymphocyte reaction, which measures lymphocyte proliferation (Goto et al., J. Antibiot., 35:1286, 1982), and screens for macrophage activation (Tanida et al., J. Antibiot. 42:1619, 1989). Inhibitors of T cell activation can be identified by growing cultured T cells (e.g., By 155.16 cells; Sleckman et al., Nature 328:351, 1987) in the presence of the candidate extract, crosslinking with activating agents, such as antibodies to CD3 and CD4 surface molecules and a secondary antibody, which normally activate T cells, and determining the level of T cell activation. T cell activation can be quantified by, e.g., a bioassay in which IL-2 production is measured by applying the T cell culture supernatant to CTLL-20 cells, which require IL-2 to live (Sleckman et al., Nature 328:351, 1987).

Extracts found to possess immunosuppressive activity in the cell culture assays can be further tested in animal model systems. An extract containing a candidate compound is administered to an immunocompetent animal, for example, a mouse which has a non-MHC matched skin graft, and the effect of the compound on, e.g., T cell or macrophage activation is determined by monitoring the immune response of the mouse.

As mentioned above, preferable screening assays are designed to identify biological activities directed specifically against the target cell, e.g., an infectious pathogen or a tumor cell, and not cells of the host organism, in order to decrease the likelihood of toxicity problems. Especially in cases where the potential therapeutic biological activity is directed against a process or structure which may be similar in the target cell and the host, it is critical to determine the relationship between the effectiveness and the toxicity of the treatment. This can be determined by standard methods using both cell culture assays and animal model systems (Goodman and Gilman's The Pharmacological Basis of Therapeutics (Goodman Gilman et al., eds.) MacMillan Publishing, New York, 1980, pp. 28–39, and 1602–1614).

Identification of Compounds Responsible for the Biological Activities

The biological activity can be further characterized by purifying the compound(s) responsible for the activity using standard methods, such as liquid-liquid, liquid-solid, or affinity chromatography with normal phase, reverse-phase, ion-exchange, and gel filtration techniques being implemented as needed (Box, S. J., Approaches to the isolation of an unidentified microbial product, in *Discovery and Isolation of Microbial Products*, Verall, M. S., Ed., Ellis Horwood, Chichester, 1985; Franco et al., Crit. Rev. in Biotech. 11(3):193–276, 1991). The purification can be monitored by co-fractionation of the biological activity, using any of the screening assays described above. Once purified, the structure of the compound can be determined using standard methods, including nuclear magnetic resonance, mass spectroscopy, and X-ray crystallography (Aszalos, A., Ed., *Modern Analysis of Antibiotics*, Marcel Dekker, New York, 1986; Franco et al., Crit. Rev. in Biotech. 11(3):193–276, 1991).

The following example is meant to illustrate, but not limit, the methods of the present invention. Other modifications and adaptations of the variety of conditions and parameters of mycology which are obvious to those skilled in the art are within the spirit and the scope of the present invention.

EXAMPLE

Sexual Cross Between *N. Nidulans* Strains D34-2 and R99

The strains of *A. nidulans* used (D34–2 and R99) are from the British strains 34 (VgI group "D") and 99 (VgI group "R"). Strains D34-2 and R99 were deposited with the American Type Culture Collection at 12301 Parklawn Drive, Rockville, Md. 20852 (U.S.A.) on Jul. 2, 1996, and have assigned Accession Numbers 74374 and 74373, respectively. Strain D34-2 carries a yellow conidiospore color marker and strain R99 carries a green conidiospore color marker. The different conidiospore colors were used to differentiate progeny of crossed organisms from those of selfed origin. Conidiospores from crossed individuals were expected to yield progeny of yellow color and green color in a ratio of approximately 50:50. VgI strains D34-2 and R99 of *A. nidulans* from British isolates (Geiser et al., Proc. Natl. Acad. Sci. 91:2349–2352, 1994) were germinated from spores on minimal media agar plates by incubation at 37° C. in an illuminated incubator. Minimal media consists of salts: $NaNO_3$(6g), KCl(0.52 g), $MgSO_4 \cdot 7H_2O$(0.52 g), $KH_2PO_4$ (1.52 g); trace elements: $ZnSO_4 \cdot 7H_2O$ (0.0022 g), $H_3BO_3$(0.0011 g), $MnCl_2 \cdot 4H_2O$ (0.0005 g), $FeSO_4 \cdot 7H_2O$ (0.0005 g), $COCl_2 \cdot 5H_2O$ (0.00016 g), $CuSO_4 \cdot 5H_2O$ (0.00016 g), $(NH_4)_6Mo_7O_{24} \cdot 4H_2O$ (0.00011 g), $Na_4EDTA$(0.005 g), per liter of water, and 1% D-glucose. Bacto-agar (1.5 %) (Difco) is included with the above-listed ingredients for making minimal media plates. The pH is adjusted to 6.5 with KOH. All subsequent incubations were carried out in a similar manner unless otherwise specified. The cultures were allowed to cross by inoculation of strain D34-2 and strain R99 on an agar plate containing minimal medium. In order to initiate the sexual cycle of reproduction, the cultures were first incubated at 37° C. for 3 days to allow merging of the mycelia. The agar plates were then sealed with paper tape to restrict the diffusion of oxygen to initiate sexual reproductive events. Additional incubation at 37° C. for 14 days was allowed for development of the reproductive structures to be completed. The appearance of a zone between the two growing strains where mycelia were merging was clearly noticeable during the incubation period. When harvesting of reproductive structures began, specimens were taken exclusively from this region.

Harvested reproductive structures were cleaned of surrounding mycelia and cells by manipulation with a needle on a sterile agar surface. Cleaned reproductive structures were then transferred to a sterile Eppendorf tube, ruptured by compression with a needle, and the ascospores resuspended in 100 µl of 0.6% sterile saline solution by vortexing.

Outgrowth of Ascospores

A 10 µl sample of the ascospore suspension in 0.6% saline was spread on a minimal media-agar plate in order to assess the outcome of the cross. Plates showing approximately equal numbers of yellow and green spore color progeny were judged to be successful crosses and the remaining suspension was spread onto plates for isolation of single colonies.

Agar plates containing 0.05% triton X-100 (Sigma) in minimal medium were inoculated by spreading 20 µl of the remaining ascospore suspension. Spores were allowed to germinate at 37° C. in an illuminated incubator. Isolated colonies were noted after 2.5 days. Some diversity in the size of the colonies from the agar plates was noted. Plates were removed from incubation, wrapped with parafilm and stored at 4° C. to prevent further growth.

Isolated colonies were transferred to 96 well microtiter plates containing 200 µl of minimal agar medium per well. Growth was carried out at 37° C. in an illuminated incubator. Growing colonies were then transferred to agar slants to scale up growth for inoculation of liquid culture.

Fermentation of D34- 2 ×R99 progeny

Corn steep liquor (CSL), (Sigma) and corn meal media (CM) were used as fermentation media. CSL media consists of 0.2% dextrose, 5.0% corn steep (Sigma) (by weight), and 0.1% yeast extract (Difco). The pH is adjusted to 6.0 using KOH. CM media consists of identical components to CSL, except that corn meal (5% by weight) is added in place of corn steep. Conical baffled flasks (250 ml) were inoculated with 5 ml spore suspension derived from agar slants and 50 ml of media. The flasks were shaken on a rotary shaker at 300 rpm and 30° C. in an illuminated growth chamber for one week. Extensive variation in mycelial development was noted during the growth. In some cultures, the mycelia rolled into small beads and in others remained more diffuse. The cultures became quite viscous as growth progressed. A wide range of coloration in the media was also noted. This suggested a diversity in metabolites secreted in the cultures.

Harvesting and Extraction of the Media

Before extraction, whole broth cultures were homogenized to break up mycelia. Butanol was used to extract a portion of the broth to provide material for metabolite screening. The remaining unextracted homogenate was kept at 4° C. and used for additional screening.

Assay for Enhanced Anti-Bacterial Production by the Progeny of D34-2 ×R99

*Bacillus subtilis* was used as a test strain for anti-bacterial production. A 25 ml overnight culture of *B. subtilis* (strain 1A1;168, tryp- from the *B. subtilis* Genetics Stock Center, Dept. of Biochemistry, Ohio State University, Columbus, Ohio 43210) in Luria broth (LB) medium was subcultured as a 1% inoculum into fresh LB medium and allowed to reach an optical density at 650 nm of 1–1.5. The culture was centrifuged at 9000 ×g for 5 minutes at 30° C. The supernatant was decanted leaving about 1 ml of spent broth behind. The cell pellet was resuspended by vortexing followed by addition of LB-0.7% agar (top agar) solution at 50° C. to bring the final volume to 25 ml. The top agar suspension was then spread onto a 20 cm² plate and allowed to cool. Ten µl of the homogenized extracts (containing no butanol) from the fermented progeny were spotted onto the plate and allowed to dry for 5 minutes. The plate was covered and set to incubate at 37° C. After 3 hours the plates were checked for growth and signs of lysis zones around the areas spotted with whole broth or unextracted homogenate. Several lysis zones were easily seen and were tabulated by measuring their diameter (Table 1).

The parental strains (D34-2 and R99) showed very low levels of anti-bacterial production, as indicated by the small diameters of the lysis zones around them. Several progeny showed enhanced production, while other progeny lacked any detectable areas of lysis. This suggests that among certain of the progeny there is enhanced production of anti-bacterial activity as a result of the cross, in agreement with the findings of Merrick (Merrick, M. J., J. Gen. Micro. 91:278–286, 1975; ibid, 287–294).

Detection of New Biological Activities in Progeny of Crosses

The results from screens for antibiotic (*B. Subtilis* lysis zone), anti-Candida (CAND & CALB), anti-Candida cell wall synthesis (CCHI), and inhibition of microtubule assembly (STUB) activities from extracts of cultures of parental and progeny strains are summarized in Table 1. The Myco ID numbers in bold represent selected progeny which tested positive in initial assays and retested positive after re-fermentation. Parental strains were fermented each time as controls. Notably, while neither parent demonstrated any detectable anti-Candida activity, several progeny did exhibit anti-Candida activity, which has remained present in a variety of fermentation media through several repeated fermentations (AA01786, AA01796, for example). In some cases, there was a coincidence between detection of CALB, CCHI, and CAND anti-Candida activities and antibiotic activity (AA01796, and AA01783, for example). However, there are numerous cases (AA01782, AA01786, AA01794, and AA02303, for example) in which there is no coincidence between the CAND, CCHI, or CALB activities and the STUB or larger lysis zones of anti-bacterial activities. Therefore, we maintain that the activities attributable to CALB, CAND, and CCHI are not detected in the parents and are not due to the compounds giving rise to the anti-bacterial and the anti-microtubule assembly activity (STUB). These observations indicate that the anti-Candida activities detected in some of the progeny were produced as a new activity as a result of the sexual mating, and is not related to the enhanced antibiotic or the STUB activity or present in either parental strain.

Figure 1A:
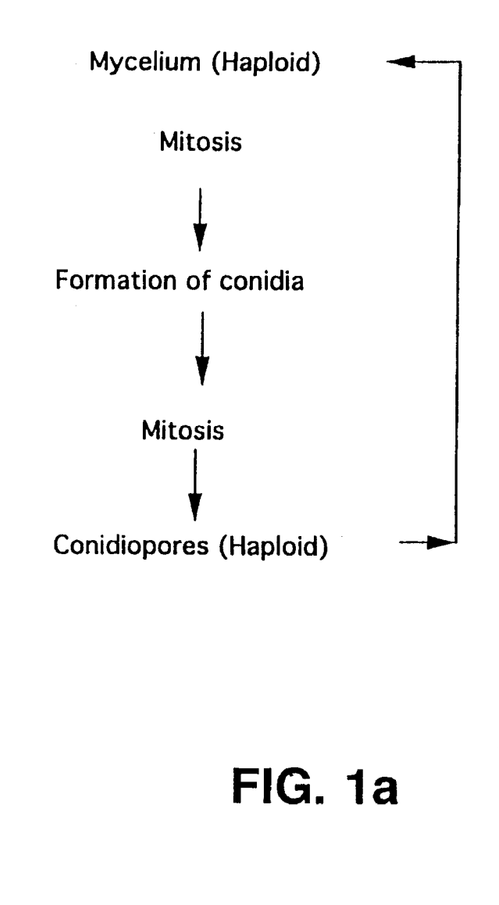
FIGS. 1A and 1B are schematic representations of asexual and parasexual reproduction in filamentous fungi, respectively.
Figure 1B:
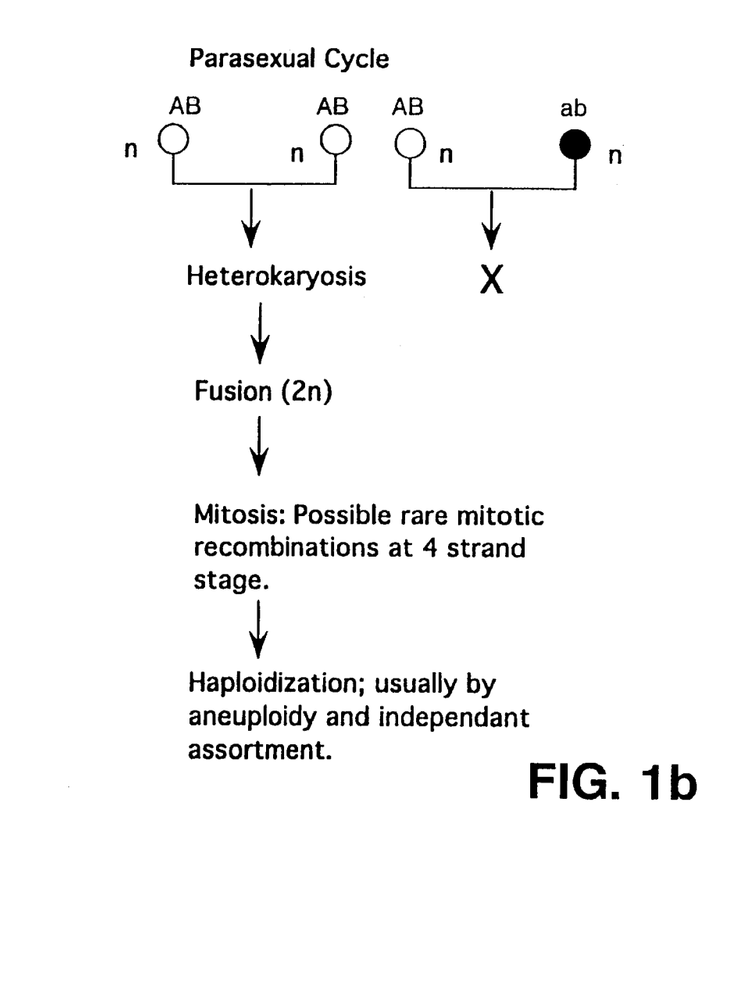
Figure 2:
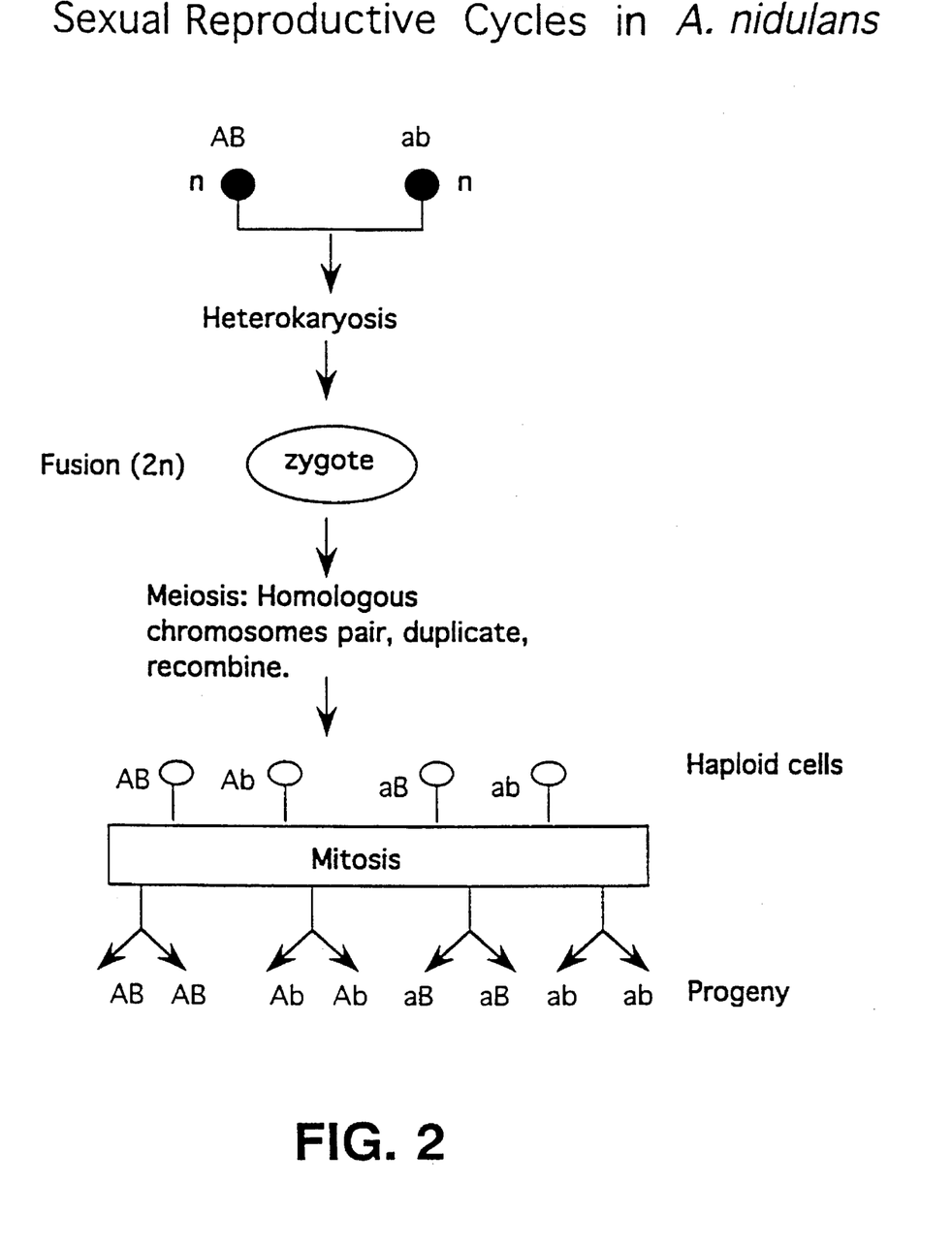
FIG. 2 is a schematic representation of the sexual cycle in a filamentous fungus (*Aspergillus nidulans*). The diploid zygote undergoes haploidization by meiosis, during which recombination between homologous chromosomes occurs. The resulting progeny thus represent new genetic VgI groups.
Figure 3:
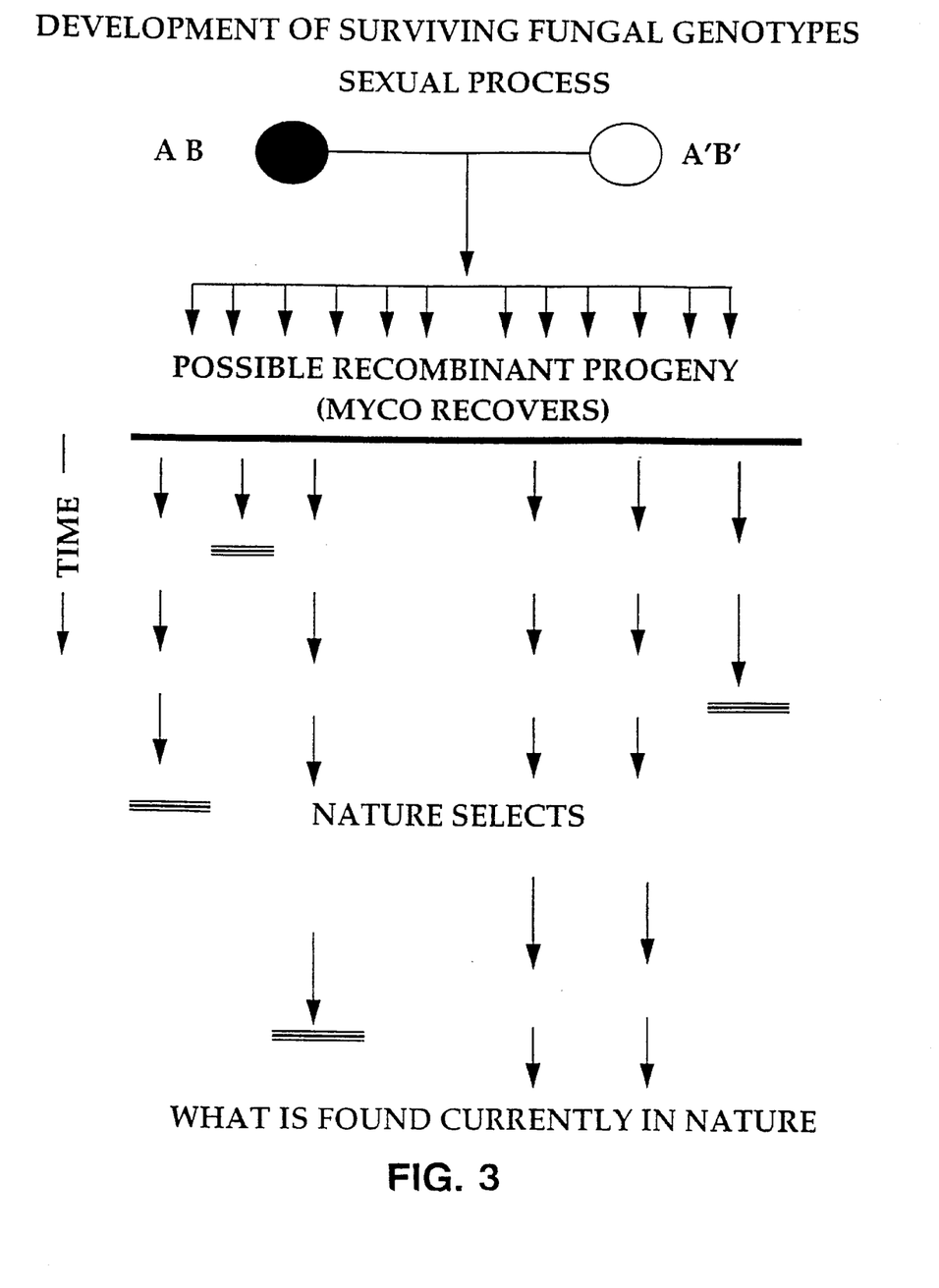
Figure 4:
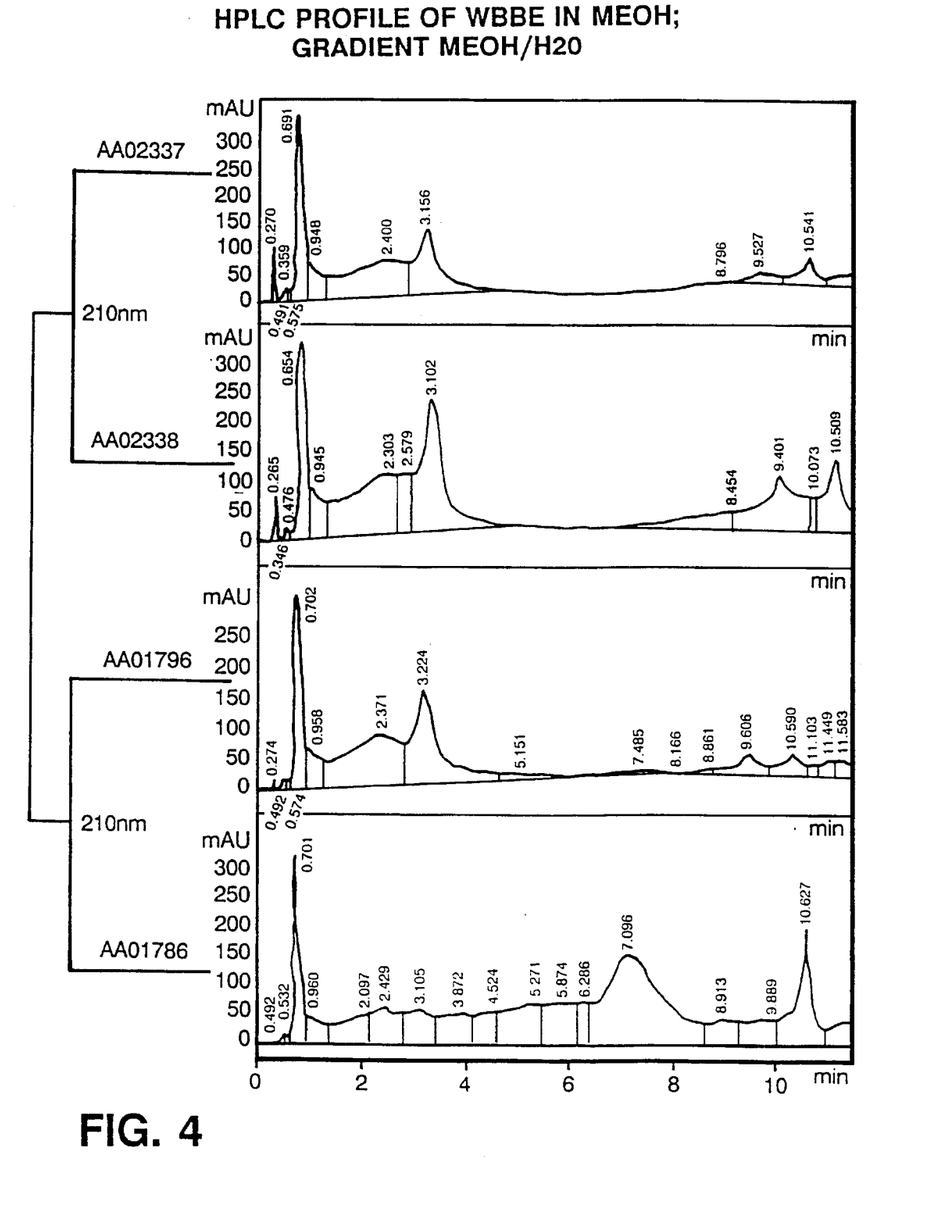
FIG. 4 is a series of graphs showing high-performance liquid chromatography (HPLC) analysis of whole broth butanol extracts (WBBEs) prepared from cultures of parental strains AA02337 and AA02338, and two of the progeny from a cross between these strains, AA01796 and AA01786. The graphs depict chromatographic differences in the contents of the WBBEs prepared from parents and progeny grown under identical conditions of media, temperature, aeration, and fermentation time.

HPLC Analysis of Whole Broth Butanol Extracts (WBBEs) Prepared From Progeny of the D34-2×R99 cross Ten of the progeny from D34-2 ×R99 were selected and refermented in three separate media for the purpose of obtaining WBBEs for reassay of biological anti-Candida activity and for HPLC analysis of the WBBE. HPLC samples were prepared by taking 2 ml portions of WBBE to dryness. Samples were dried to 500 µ vacuum and then resuspended in 500 µl of HPLC-grade methanol followed by 5 minutes in a sonic water bath. HPLC analysis was carried out with a 5 cm C-18 reversed phase column using a stepped gradient beginning with 90% water and 10% methanol, and proceeding to 85, 75, 60, 50, 20% water over 30 minutes. Flow was 1 ml per minute and elution was monitored at 210 nm. Retention times for the components of the parental and two progeny WBBEs showed marked difference between parents and the progeny. Both parents had large gaps in the elution profile segments between 0 and 10 minutes retention time (FIG. 4). FIG. 4 shows both parents (AA02337-4 and AA02338-4) and a representative scan of two progeny (AA01786-4 and AA01796-4; the -4 signifies the CM media used in fermentation). This data reinforces that presented in Table 1 which shows that metabolites not present in the parental fermentations appear in the fermentation broths of the progeny, and that there is significant variation among the progeny as well.

Thus, we have demonstrated that sexual crosses of VgI strains of fungi results in the production of new progeny. These isolates may be propagated by fermentation culture in order to produce new biologically active secondary metabolites not present in the parental strains.

Other Embodiments

The above example is to be construed as merely illustrative, and not limitative of the remainder of the disclosure in any way whatsoever.

From the above description, one skilled in the art can easily ascertain the essential characteristics of the present invention, and without departing from the spirit and scope thereof, can make various changes and modifications of the invention to adapt it to various usages and conditions. All publications cited herein are fully incorporated by reference herein in their entirety. Other embodiments are in the claims set forth below.

TABLE 1

Summary of Progeny and Parent organisms

| Myco ID Number | Spore Color | *B. Subtilis* Lysis Zone (mm) | STUB | CAND | CCHI | CALB |
|---|---|---|---|---|---|---|
| AA01769 | y | n | | | | |
| AA01770 | y | n | | | | |
| AA01771 | y | n | | | | |
| AA01772 | g | n | | | | |
| AA01773 | y | 7 | | x | | |
| AA01774 | g | n | | x | | |
| AA01775 | y | 5 | | x | | |

TABLE 1-continued

Summary of Progeny and Parent organisms

| Myco ID Number | Spore Color | B. Subtilis Lysis Zone (mm) | STUB | CAND | CCHI | CALB |
|---|---|---|---|---|---|---|
| AA01776 | y | 7 | x | x | | |
| AA01777 | g | n | | x | | |
| AA01778 | y | 7 | | | | |
| AA01779 | y | n | | | | |
| AA01780 | y | 5 | | x | | |
| AA01781 | g | 7 | | | | |
| AA01782 | y | 7 | | | | |
| AA01783 | y | 9 | | x | x | x |
| AA01784 | g | n | | | | |
| AA01785 | g | 8 | | | | |
| AA01786 | y | n | | x | x | x |
| AA01787 | y | n | | | | |
| AA01788 | g | 7 | | | | |
| AA01789 | y | n | | | | |
| AA01790 | y | 6 | | | | |
| AA01791 | y | 9 | | | | |
| AA01792 | g | 7 | | | | |
| AA01793 | g | 6 | | | x | x |
| AA01794 | g | 8 | | | | |
| AA01795 | g | 8 | | | | |
| AA01796 | g | 8.5 | | x | x | x |
| AA01797 | g | 6 | | | | |
| AA01798 | g | 7.5 | | x | | |
| AA01799 | g | n | | x | | |
| AA01800 | g | n | | x | | |
| AA01801 | g | n | x | x | | |
| AA01802 | y | n | | x | | |
| AA01803 | y | n | | | | |
| AA01804 | g | n | | | | |
| AA01805 | g | n | | x | | |
| AA01806 | y | n | | x | | x |
| AA01807 | g | 6 | | | | |
| AA01808 | g | 6 | | | | |
| AA01809 | g | 6 | | | | |
| AA01810 | g | n | | | | |
| AA01811 | g | n | | x | | |
| AA01812 | y | n | | x | | |
| AA01813 | y | 6 | | | | |
| AA01814 | g | n | | x | | |
| AA01815 | g | 6 | | | | |
| AA01816 | y | 9 | | | | |
| AA01817 | g | n | | | | |
| AA01818 | g | n | x | | | |
| AA01819 | y | 6 | | | | |
| AA01820 | y | 8 | | x | | |
| AA01821 | y | n | x | | | |
| AA01822 | y | 7 | | | | |
| AA01823 | y | n | | x | | |
| AA01824 | y | n | | | | |
| AA01825 | g | 8 | | | | |
| AA01826 | y | n | x | x | | |
| AA01827 | g | 9 | x | x | | |
| AA01828 | y | 9 | | | | |
| AA01829 | y | 8.5 | | | | |
| AA01830 | y | n | | x | | |
| AA01831 | g | n | x | | | |
| AA01832 | y | 8 | | | | |
| AA01833 | y | 8.5 | | | | |
| AA01834 | y | 8 | | x | | |
| AA01835 | g | 8 | | | x | x |
| AA01836 | y | n | | | | |
| AA02284 | g | n | | | | |
| AA02285 | g | n | | | | |
| AA02286 | y | n | | x | | |
| AA02287 | g | n | | | | |
| AA02288 | g | n | | | | |
| AA02289 | g | n | | | | |
| AA02290 | y | 6 | | | | |
| AA02291 | g | 6 | | | | |
| AA02292 | g | n | | | | |
| AA02293 | g | 6 | | x | | |
| AA02294 | g | n | | x | | |
| AA02295 | y | n | | | | |
| AA02296 | y | 5 | | | | |

TABLE 1-continued

Summary of Progeny and Parent organisms

| Myco ID Number | Spore Color | B. Subtilis Lysis Zone (mm) | STUB | CAND | CCHI | CALB |
|---|---|---|---|---|---|---|
| AA02297 | y | n | | | | |
| AA02298 | g | n | | | | |
| AA02299 | g | n | | | | |
| AA02300 | g | n | | | | |
| AA02301 | g | n | | | | |
| AA02302 | g | n | | | | |
| AA02303 | y | 7 | | | | |
| AA02304 | y | n | | | | |
| AA02305 | y | n | | x | | |
| AA02306 | y | n | x | x | | |
| AA02307 | y | n | | | | |
| AA02308 | y | p | | | | |
| AA02309 | y | n | | | | |
| AA02310 | y | p | x | x | | |
| AA02311 | y | n | x | | | |
| AA02312 | y | 3 | | | | |
| AA02313 | y | n | | | | |
| AA02314 | g | n | | | | |
| AA02315 | y | n | | x | | |
| AA02316 | g | n | x | x | x | x |
| AA02317 | y | n | | x | | |
| AA02318 | y | n | | x | | |
| AA02319 | y | n | | | | |
| AA02320 | y | n | | | | |
| AA02321 | y | 3 | | x | | |
| AA02322 | y | n | | x | | |
| AA02323 | y | n | | | | |
| AA02324 | g | n | | | | |
| AA02325 | y | n | | | | |
| AA02326 | y | n | | | | |
| AA02327 | y | n | | x | | |
| AA02328 | g | n | | x | | |
| AA02329 | g | 5 | | | | |
| AA02330 | g | n | | | | |
| AA02331 | g | n | | | | |
| AA02332 | g | n | | | | |
| AA02333 | g | n | | | | |
| AA02334 | y | 6 | | x | | |
| AA02335 | g | n | | | | |
| AA02336 | y | n | | | | |
| AA02337* | g | <3 | x | | | |
| AA02338* | y | <3 | x | | | |

*-Parent Organism
y = yellow, g = green; n = no lysis detected; x = Activity in screen

We claim:
1. A process for producing fungal strains which produce biologically active secondary metabolites in detectable amounts, comprising the steps of
 (a) carrying out a sexual cross between the vegetatively incompatible strains D34-2 and R99 of *Aspergillus nidulans;*
 (b) recovering the progeny produced;
 (c) culturing the progeny of said sexual cross in an aqueous nutrient medium containing assimilable sources of carbon, nitrogen and inorganic substances;
 (d) screening the progeny of said sexual cross or the cultured fermentation broth thereof for the production of biologically active secondary metabolite products having biological activity which products are not detectable upon cultivation of either said D34-2 or R99 strains under the same process conditions and using the same detection techniques as used in the screening of the progeny of said sexual cross.

* * * * *